United States Patent [19]
Burtschi

[11] 4,039,756
[45] Aug. 2, 1977

[54] ARTIFICIAL LARYNX WITH SEMI-AUTOMATIC INFLECTION CONTROL

[75] Inventor: Richard Burtschi, East Lansing, Mich.

[73] Assignee: Missouri Province Educational Institute, St. Louis, Mo.

[21] Appl. No.: 742,432

[22] Filed: Nov. 17, 1976

[51] Int. Cl.² .............................................. A61F 1/20
[52] U.S. Cl. ................................................ 179/1 AL
[58] Field of Search .............. 179/1 AL, 121 C; 3/1.3

[56] References Cited
U.S. PATENT DOCUMENTS

3,291,912  12/1966  Flanagan ........................... 179/1 AL
3,766,318  10/1973  Webb ................................ 179/1 AL Primary Examiner—Kathleen H. Claffy
Assistant Examiner—E. S. Kemeny
Attorney, Agent, or Firm—Cullen, Settle, Sloman & Cantor

[57] ABSTRACT

An artificial larynx helps people speak with less monotonous voice by providing an automatic pitch changer for voice inflection. The predetermined basic vocal pitch frequency circuit is modulated by a frequency control signal whose value changes at a predetermined rate established by an RC circuit, and includes switches manually-operable to select upward or downward pitch change inflections.

20 Claims, 5 Drawing Figures

ARTIFICIAL LARYNX WITH SEMI-AUTOMATIC INFLECTION CONTROL

BACKGROUND OF THE INVENTION

1. Field of the Invention

This invention relates to an artificial larynx and more particularly to an electrically-powered artificial larynx having pitch change capability.

2. Description of the Prior Art

Persons who have been deprived of the use of their vocal chords or larynx through paralysis or surgery for example, frequently employ a mechanical or electromechanical speech aid commonly known as an artificial larynx. The basic operating principal of such a device is to generate a tone having a fundamental frequency in the speech range of the average human voice and to introduce the tone into one of the resonant speech cavities of the user, such as the mouth or pharnyx. To speak, the user modulates the artificially-generated tone by varying the shape of the resonant speech cavities comprising the pharnyx, mouth and nose and by making the usual constrictions of the tongue, teeth and lips so as to articulate the modulated tone as human speech.

One well-known type of artificial larynx employs a tracheal tube with one end inserted into a surgically made aperture in the users throat which terminates at the users trachea. The force of accelation through the tube is applied to a reed which vibrates to produce the required tone. The sound from the vibrating reed is introduced into the mouth or nasal cavity by means of a second tube.

Another such device employs an electro-acoustic transducer which is mounted in the mouth of the user by securing it to a denture. Power from batteries is transmitted to provide an oscillatory signal which is applied to the transducer by means of a wire entering the user's mouth.

Still another type of artificial larynx employs an electromechanical vibrator adapted to be secured to or held against the outside of the users throat so as to induce a tone into the region of the pharnyx. The generated sound is transmitted through the tissues of the throat and into the mouth where it is articulated into words and phrases.

Still another type includes a sound generator which is coupled to a plastic tube or the like to transmit the generated sound into a person's mouth through the lips which are held open such that the mouth can then be used to articulate the generated sound into speech.

Each of the devices of the prior art is deficient in one or more important aspects. For example, none of the prior art devices includes a satisfactory system for controlling pitch. One device employs an arrangement designed to control pitch by varying the point of resonance in a mechanically resonant vibrator. The principal, although sound, cannot be applied effectively within the necessary limits of size and complexity. The instrumentation is therefore a compromise and the resulting changes in pitch lack the distinguishing characteristics of the human voice.

Additionally, most of the devices of the prior art lack a means for generating the basic tone within a spectrum that approximates the range of normal human speech and, accordingly, the sounds produced are defective in both tonal quality and intelligibility. Many of the systems of the prior art emply power systems requiring heavy duty batteries which must be carried by the user or fixed to his person or clothing. Such arrangements are both awkward and obstrusive and are therefore embarrassing to the user.

One of the devices of the prior art provides pitch control by providing a variable resistance in a relaxation oscillator circuit which generates the pulses to drive the transducer. This system requires operator dexterity in that the rate, the amount and the direction of pitch change must all be manually controlled as the operator increases and decreases the oscillator resistance. Use has shown that few persons are able to manipulate the rate of change of the pitch in such a manner so as to produce a pleasing, human-like quality of speech. Rather, a buzzing mechanical or computer-like sound is often produced and the manual manipulation required to control the rate of pitch change often leads to rapid increases or decreases in pitch or, in the alternative, to extremely slow or jerky, non-human sounding pitch changes.

These drawbacks of the prior art are the major reason why only about 15% of voiceless people utilize an artificial larynx. It would be extremely advantageous to humanize the sound emitted by a person using an artificial larynx by improving the tonal quality and reducing the requirements for manual dexterity and coordination so as to produce a less mechanical sounding and more human-like speech.

The present invention avoids all of the problems and disadvantages of the prior art by providing an artificial larynx which produces a more human-like tonal quality and which provides a pitch change circuit wherein the direction of pitch may be manually selected but the total amount of change and the rate of change is pre-established so as to eliminate the users need for manual dexterity and insure the generation of a less monotonous, more human-like quality in the resulting speech.

BRIEF SUMMARY OF THE INVENTION

This invention provides an artificial larynx having means for generating electrical pulses at a predetermined frequency in the average fundamental frequency range of the human voice. A transducer means is provided for vibrating at the predetermined basic frequency to generate sound waves which can be articulated in a person's speech cavities for speech purposes. An electrical driver responsive to the generated electrical pulses is used to drive the transducer means. A pitch change circuit is provided which includes RC circuit means for generating a frequency control signal whose value varies at a predetermined rate established by the RC time constant of the circuit. The frequency control signal is supplied to the pulse-generating means so that the rate of change of the value of the frequency control signal determines the rate at which the frequency of generation of the electrical pulses changes. Manually-operable switching means are coupled to the RC circuit means for enabling the person to selectively increase the value of the control signal so as to increase the frequency of generation of the electrical pulses at the established predetermined rate or for enabling a person to selectively decrease the value of the control signal so as to decrease the frequency of generation of the electrical pulses at the established predetermined rate thereby permitting the person to select a direction of inflextion in the pitch of the sounds articulated in his speech cavities without his having to worry about jerky machine-like variations resulting from less than ideal manual manipulations in the rate.

The pitch change control circuit of the present invention employs an RC circuit means including resistive means and capacitive means which may be adjusted or selected to establish a predetermined RC time constant. This time constant determines the rate at which the pitch changes automatically thereby freeing the operator from having to utilize manual manipulation of a knob or the like for controlling the rate of change of pitch. The time constant can be chosen to meet the needs of the individual user so as to produce a pitch change which automatically varies at a predetermined rate to render that person's speech less machine-like, less monotonous, and more nearly normal.

The automatic variation of the rate of change of pitch avoids the manual dexterity problems of selecting and controlling the rate of pitch change inherent in the prior art devices. This avoids the rough, jerky pitch changes whic cause the prior art devices to produce a computer-like sound. Accordingly, this invention eliminates a serious prior art limitation and gives the simulated speech a more pleasing and natural quality and an improved clarity. This invention gives the user of an artificial larynx the choice of direction of the pitch change but leaves the actual changing of the pitch and the determination of the rate of change up to the circuitry of the instrument itself. The resulting speech is more natural because the user is able to concentrate more on what he is saying rather than on how to say it and how to manipulate control knobs with his fingers while doing so.

The pitch is extremely important because when people speak and wish to emphasize a point they will vary the pitch of their voice in a desired direction. For example, to say "no" with an upward inflection can produce a different meaning than saying no with a downward inflection. The few prior art devices capable of varying pitch at all require the manual adjustment or movement of a control knob or member each increment of which changes pitch a particular amount. This gives the speaker the conscience responsibility for manually varying the pitch of his voice which amounts to giving him primary responsibility for what is really of secondary importance in normal speaking. That is, automatic pitch variation more nearly approaches normal speech because it offers the speaker a simple choice, i.e., the choice of direction of the pitch variation. The amount of change, the rate of change, and the final value of the pitch is left up to automatic circuitry. The undesirable requirement for continual manual control of pitch change and rate of change has been eliminated and automatic bi-directional control has been achieved by the artificial larynx of the present invention.

The pitch change circuit of the present invention employs an RC circuit whose RC time constant controls the rate of change in pitch automatically. The circuit may be provided with means for varying the RC time constant so as to establish a different predetermined rate of pitch change if such is required to meet the needs of the individual. But, in the preferred embodiment hereof, this would be an internal adjustment and would not be a parameter requiring continuous control by the user. In normal circumstances, a one-time adjustment to achieve a suitable rate would be sufficient.

Additionally, the pulse-generating means of the present invention is an inexpensive, compact, highly reliable circuit capable of precisely producing a train of pulses at a control rate to insure superior tonal qualities.

In the preferred embodiment, the pulse-generating means employs a second RC circuit for normally establishing the frequency of generation of electrical pulses in the average fundamental frequency range of a human voice so as to insure more normal speech. Means may be provided in the RC circuit for adjusting its time constant for varying the normally established or basic frequency of generation of the electrical pulses to meet the needs of the individual. For example, a first circuit path may be provided in the RC circuit for establishing the normal frequency of generation of the electrical pulses in the average fundamental frequency range of a male human voice while a second parallel path may be selected in the RC circuit for normally establishing the frequency of generation of the electrical pulses in the average fundamental frequency range of a female human voice, as desired.

Furthermore, in the preferred embodiment of the present invention, the transducer means may include a coil and a capacitive means connected across the coil for introducing desireable harmonics into the sound generated by the transducer means to eliminate mechanical-sounding monotones and produce more human-sounding speech.

A means responsive to the generated pulses for driving the transducer means of the present invention may include means for selectively increasing and decreasing the volume of sound outputted from the transducer means. This could, for example, be effected by a variable resistor or, in the alternative, a pair of parallel branches could be provided having a different impedances with means for selecting one or the other of the branches to produce either a high volume sound or a low volume sound depending upon the environment in which the person is attempting to speak.

Other advantages and meritorious features of the present invention will be more fully understood from the following detailed description of the drawings and the preferred embodiment, the appended claims and the drawings which are briefly described hereinbelow.

DESCRIPTION OF THE PREFERRED EMBODIMENTS

Figure 1:
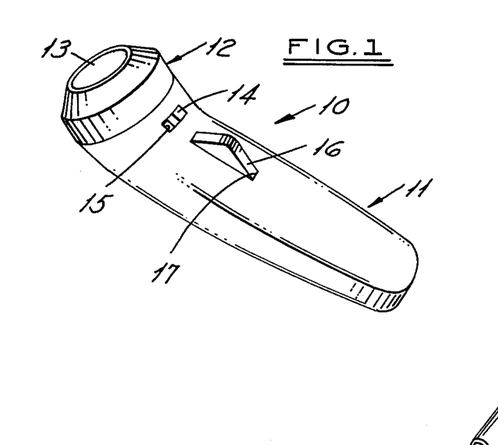
FIG. 1 is a front perspective view of the exterior of a typical artificial larynx which may embody the circuitry of the present invention.

FIG. 1 shows an artificial larynx 10 having a body portion and a forward end portion 12 which houses a vibrating disk 13 which may be placed against a person's throat to produce sound which is supplied from the throat to the mouth where it can be articulated into words. The body portion 11 of the artificial larynx 10 of FIG. 1 includes an on-off switch 14 which extends through an aperture 15 in the body 11 and a two-position control switch 16 which extends through an aperture 17 in the body portion 11 for manually selecting the direction of pitch change as hereinafter described.

Figure 2:
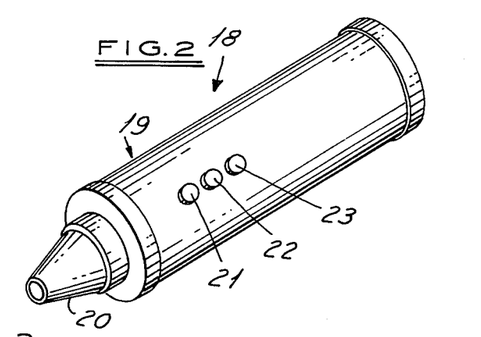
FIG. 2 is a perspective view of the exterior of another embodiment of the artificial larynx of the present invention.

FIG. 2 shows another embodiment of an artificial larynx 18 having a body portion 19 which contains a conventional vibrating element (not shown) which emits sound waves through the tone portion 20 directly into a persons mouth where the sound waves may be articulated into words and phrases. The housing 18 is shown as including a first on-off push button 21 and second and third push button switches 22, 23 which can be used to select the direction of pitch change as hereinafter described. The particular design of the housing 11, or 19 of the artificial larynx of the present invention and the particular structure and operation of the transducer means used to generate the basic sound wave is conventional and any structure compatible with applicant's circuitry may be employed.

Figures 3, 4, 5:
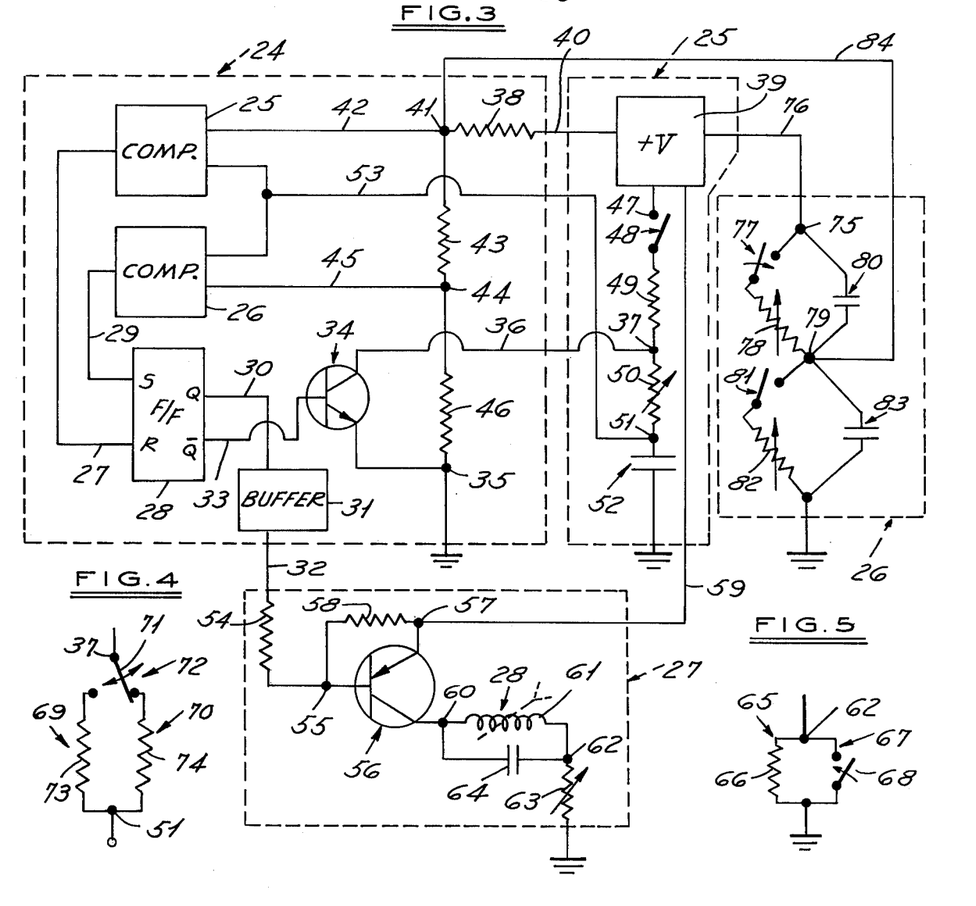
FIG. 3 is an electrical schematic diagram, partially in block form, of the artificial larynx of the present invention including the pitch control circuitry therefore.
FIG. 4 is an electrical schematic diagram of an alternate circuit which may be substituted for resistor 50 of FIG. 3.
FIG. 5 is an electrical schematic diagram of an alternate circuit which may be substituted for resistor 63 of FIG. 3.

FIG. 3 is an electrical schematic diagram of the artificial larynx 10 or 18 of the present invention. FIG. 3 shows a pulse-generating circuit generally represented by reference numeral 24, an RC network 25 associated with the pulse-generating circuit 24 for establishing the normal frequency at which the electrical output pulses are generated, a pitch control circuit 26 for automatically controlling the amount and rate of pitch change and for manually selecting the direction thereof, and transducer circuitry 27 which includes a conventional vibratory transducer 28 and the drive circuitry therefore.

The pulse-generating circuit 24 includes a first conventional comparator 25 and a second conventional comparator 26. The comparators 25 and 26 each have first and second comparator inputs and a comparator output. The output of the first comparator 25 is connected via lead 27 to the Reset input of a conventional RS flip-flop 28 or some similar bistable device. The output of the second comparator 26 is connected to the Set input of flip flop 28 via lead 29. The Q output of the flip-flop 28 is connected via lead 30 to the buffer block 31 which contains conventional frequency stabilization circuitry for isolating the pulse-generating circuitry 24 from load fluctuations. The electrical output pulses outputted by the flip-flop 28 are buffered and then supplied via lead 32 to the transducer circuitry 27 as hereinafter described.

The $\overline{Q}$ output of the flip-flop 28 is connected via lead 33 to the base electrode of an NPN transitor 34 having its emitter connected to a grounded node 35 and its collector connected via lead 36 to a node 37. The pulse-generating circuitry 24 also includes a voltage divider network which includes a first resistor 38 having one end connected to a power supply 39 via lead 40 and its opposite and connected to a first voltage tap node 41. Node 41 is connected directly to the first or reference input of the first comparator 25 via lead 42 and to one end of a second voltage divider resistor 43 whose opposite end is connected to a second voltage tap node 44. Node 44 is connected directly to the first or reference input of the econd comparator 26 via lead 45 and to one end of a third voltage divider resistor 46 whose opposite end is connected to the grounded node 35.

The RC circuitry 25 associated with the pulse-generating circuitry 24 includes the power supply or source of potential 39 which, in the preferred embodiment disclosed herein, may be a conventional nine-volt battery. An output of the power supply is connected to one terminal 47 of a normally-open switch 48 which can be used as an on-off switch to control when sound waves are to be generated. The switch 48 may correspond, for example, to the switch 14 of FIG. 1 and to the push button switch 21 of FIG. 2. The opposite terminal of the switch 48 is connected to one end of a first charging resistor 49 whose opposite end is connected to a discharge node 37. Node 37 is connected to one end of a resistance means 50 which may be, for example, a variable resistor or the like which has its opposite end connected to a monitored signal node 51. Node 51 is connected to one plate of a charging capacitor 52 whose opposite plate is connected directly to ground. The monitored signal which is taken from node 51 represents the charge stored on the capacitor 52 and is supplied via lead 53 to the second inputs of the comparators 25, 26 for comparison with the reference signals present at the first inputs.

The basic operation of the pulse-generating circuit 24 will now be briefly described. The three serially connected voltage divider resistors 38, 43 and 46 are connected between the nine volt power supply 39 and ground. If the value of the resistances is equal, then about ⅔ of the supply voltage or 6 volts will be present at node 41 and about ⅓ of the supply voltage or 3 volts will be present at node 44. Node 41 is connected via lead 42 to the first or reference input of the first comparator 25 so as to supply a first reference signal thereto. The second voltage tap node 44 is connected via lead 45 to the first or reference input of the second comparator 26 to supply a second reference signal thereto. The signal present at the node 51 at the positive plate of the capacitor 52 is the signal monitored by the comparators 25 and 26 and this signal is supplied via lead 53 to the second inputs of comparators 25 and 26.

When the switch 48 is closed to turn the artificial larynx of FIG. 3 on, power is supplied from the source 39 to the RC series branch comprising charging resistor 49, variable resistor 50 and the charging capacitor 52. Assuming that the discharge transitor 34 is initially in the non-conductive state since a "low" signal is present at the $\overline{Q}$ output of flip-flop 28, the charging capacitor 52 will begin to charge toward the value of the supply voltage at a rate determined by the RC time constant of the circuit. The RC time constant, of course, is determined by the component value of resistors 49 and 50 and the capacitance of the charging capacitor 52. The RC time constant is initially established, as by choosing component values or altering the resistance of variable resistance 50, so as to produce electrical output pulses at a normal or basic frequency within the frequency range of the average human voice. The increasing and decreasing monitored signal present at node 51 is supplied via lead 53 to the second or monitored inputs of the comparators 25 and 26 for comparison with the first and second reference signals present at the first inputs of the comparators 25 and 26 respectively.

Assume that the flip-flop 28 is normally initialized when the on-off switch 28 is closed so as to be placed in a first state in which the $\overline{Q}$ output is "high" and the Q output is "low". This first state of the flip-flop 28 supplies a high signal via lead 30 to the output buffer 31 and a low signal to discharge transitor 34 for keeping the discharge transitor 34 in the non-conductive state so as to allow the charging capacitor 52 to charge through resistors 49 and 50. As the charge on the capacitor 52 reaches or exceeds the value of the first reference signal, the output of the first comparator 25 will go low and this first triggering signal will be supplied to the Reset input of flip-flop 28 causing the flip-flop 28 to switch to the opposite state so as to cause the Q output to go low and the $\overline{Q}$ output to go high. The high signal from the $\overline{Q}$ output is supplied via lead 33 to the base of discharge transistor 34 causing it to conduct and complete a discharge path between the positive plate of capacitor 52 and grounding node 35 via resistor 50 and the conductive discharge transistor 34.

As the value of the monitored signal at node 51 decreases, it will reach or fall below the second reference signal causing the output of comparator 26 to go low. This output or second triggering signal is supplied to the Set input of flip-flop 28 to restore the flip-flop to the first state thereby turning off the transitor 34 to allow the charging capacitor 52 to begin to charge again. Hence, it will be seen that the values of the first and second reference signals established by the voltage divider network comprising resistors 38, 43 and 46 and the RC time constant of the circuit comprising resistors 49, 50 and capacitor 52 estabishes the rate of generation of the first and second triggering signals outputted from the comparators 25 and 26 thereby determining the rate at which the flip-flop 28 changes states. The rate at which flip-flop 28 changes states determines the frequency of generation of electrical output pulses from the output buffer 31 via lead 32 and, as previously described, the RC time constant of the circuit 25 may be initially selected so as to choose a base frequency of generation of the output pulses at a rate within the frequency range of the average human voice.

The train of buffered electrical output pulses is supplied via lead 32 through a resistor 54 to the base node 55 of a PNP power transistor 56. The emitter electrode of power transistor 56 is taken from node 57. Node 57 is connected through a biasing resistor 58 to the base node 55 and through lead 59 to the positive power supply 39. The collector of power transistor 36 is taken from node 60 which is connected to a transducer means 28 represented by the oscillator coil 61 whose opposite end is connected to node 62. Node 62 is connected to ground through a variable resistor 63 which may be used to increase or decrease the impedance of the circuit for volume control purposes. A capacitor 64 may be connected across the coil 61 of the transducer means 28 in parallel therewith to introduce desireable harmonics into the output of the transducer means 28 for eliminating mechanical-sounding monotones and producing a more human-like quality to the resulting speech. Various types of conventional transducer means 28 may be employed with the present invention.

The variable resistor 63 of the transducer block 27 of FIG. 3 may be replaced with the circuit of FIG. 5 or an equivalent thereof if desired. The circuit of FIG. 5 shows the common node 62 but the resistance 63 of FIG. 3 has been replaced by the parallel combination of a first circuit branch 65 having a resistor 66 of a first value connected between the node 62 and ground. A second parallel branch 67 including a first manually-operable switch 68 in series therewith is connected between node 62 and ground so that when the user of the artificial larynx 10, or 18 of the present invention is an environment in which he does not desire to generate a high volume or loud signal, the switch 68 is opened so that the resistor 66 completes the circuit path to ground and produces a low volume output from the transducer means 28 of FIG. 3. Alternatively, when the user is in an environment requiring a higher volumn of sound, the switch 68 can be closed thereby completing a low impedance path between node 62 and ground so as to produce a high volume or loud output from the transducer means 28 of FIG. 3.

Similarly, as previously described, the variable resistor 50 of the RC circuit 25 of FIG. 3 may be replaced with the circuit of FIG. 4. The discharge node 37 may be coupled to the signal monitoring node 51 via a pair of parallel circuit branches 69, 70. The first circuit branch 69 includes a resistor of 73 of a first resistive value connected between a first switch terminal and the node 51 and the second branch 70 includes a second resistor 74 of a second resistive value connected between a second switch contact and the node 51. When the wiper arm 71 of the switch 72 is positioned to complete a current path between node 37 and the first branch 69 through the first resistor 73, a first RC time constant is established for the circuit 25 which will enable the circuit 24 to output a train of pulses at a frequency generally corresponding to the average fundamental frequency of a human female voice and when the wiper arm 71 of the switch 72 is positioned so as to connect node 37 with the second branch 70, the resistor 74 is placed into the circuit and establishes a second and different RC time constant for the circuit 25 to produce a train of output pulses at lead 32 whose basic frequency is in the average frequency range of the male human voice. Therefore, the mere positioning of the wiper arm 71 of the switch 72 between the two circuit arms 69 and 70 enable the artificial larynx of FIG. 3 to be preset for optimal tone quality for either a male or a female user, as desired. Similarly, both of the resistors 73 and 74 may be variable to allow the RC time constant to be more precisely tuned to the needs of the individual male or female, as desired.

The pitch control circuit 26 of the present invention includes a first input node 75 which is connected via lead 76 to the power supply 39. Node 75 is connected through the series combination of a first manually-operable, normally-open switch 77 and a variable resistor 78 to a frequency control output node 79. A first charging capacitor 80 is connected in parallel with the series combination of the switch 77 and resistor 78 between nodes 75 and 79. Node 79 is connected to ground through the series combination of a second manually-operable, normally-opened switch 81 and a second variable resistor 82 while a second charging capacitor 83 is connected in parallel with the series combination of the switch 81 and resistor 82 between the frequency control output node 79 and ground. The frequency control output node 79 supplies a frequency control signal via lead 84 to the first voltage tap or reference node 41 of the voltage divider comprising resistors 38, 43 and 46 of the pulse generator circuit 24.

In operaton, the pitch change circuitry 26 includes an RC network. The frequency control signal taken from output node 79 has a value which increases or decreases depending upon which of the switches 77 and 81 are closed. The switches 77 and 81 could represent a rocker arm type switch such as switch 16 of FIG. 1 having a first position in which the switch 77 is closed while the switch 81 is open and a second position wherein the switch 77 is open while the switch 81 is closed. Alternatively, both switches could be normally-opened and the switch 77 could correspond to push button switch 22 of FIG. 2 while switch 81 corresponds to push button switch 23 so that both switches may be opened at the same time or individually operated by depressing the appropriate push button switches 22, 23.

When both switches are in the open position, there is no frequency control signal supplied from node 79 to the first voltage tap 41 and therefore the pitch change circuitry 26 has no effect upon the frequency of generation of the output pulses of circuit 24.

The operation of the switches 77 and 81 allow the user to manually choose the direction in which the pitch change occurs while the values of the components thereof controls the rate at which the pitch automatically changes and the total amount of pitch change. Assuming that the switch 77 is closed while the switch 81 is opened, a current path is established from the power supply 39 to ground through lead 76, input node 75, the closed switch 77, resistor 78, and the charging capacitor 83. Initially, the capacitor 83 would have no charge on its plates but it would begin to charge as soon as the switch 77 was closed. The rate at which the capacitor 83 charges and hence that the rate at which the value of the frequency control signal at node 79 increases is determined by the RC time constant determined by the component value of resistors 78 and capacitor 83. The maximum value to which the frequency control signal can increase is to the value of the supply 39 or nine volts. Therefore, the first series branch comprising the closed switch 77, the resistor 78, and the charging capacitor 83, having a first predetermined time constant, establishes the rate at which the value of the frequency control signal increases and the maximum amount of its increase and this occurs automatically once the RC time constant of the first circuit branch is established.

Resistor 78 is shown as a variable resistor for altering the RC time constant if desired but this would not normally be done on any type of continuing basis. As the frequency control signal from node 79 is supplied to the first voltage tap 41, the first reference signal supplied via lead 42 to the first input of the comparator 25 will remain unaltered until the 6 volt level of the first reference voltage normally present at node 41 is exceeded. As the frequency control signal overrides or augments the value normally present at node 41, the value of the first reference signal increases at the predetermined rate established by the RC time constant of the first series circuit of the pitch control circuitry 26. The second reference signal present at node 44 will rise similarly due to the voltage divider effect of resistors 43 and 46. The overall effect of increasing the first and second reference signals at a predetermined rate causes a continual rise in the repetition rate or frequency at which the first and second triggering signals are outputted from the comparators 25 and 26 and therefore an increase in the frequency of generation of the electrical pulses outputted from the flip-flop 28. The increase in the frequency of the outputted pulses increases the rate at which the transducer means 28 is driven by the power transistor 56 and therefore automatically increases the pitch of the sound produced by the transducer means 28.

Alternatively, if the manually operable switch 81 is closed and the switch 77 is opened after the circuit has been operating for some time, the capacitor 80 will be charged to the supply potential of nine volts and the closure of the switch 81 will establish a second RC path between the capacitor 80 and through the output node 79, the closed switch 81, the discharging resistor 82, and ground thereby allowing the capacitor 80 to discharge through the resistor 82 to decrease the value of the frequency control signal at output node 79.

Once the value of the frequency control signal which is supplied to the first voltage tap 41 drops below 6 volts, the level of the first and second reference signals supplied to the first input of the comparators 25 and 25 reduces at the rate determined by the RC time constant of the discharge circuit including capacitor 80 and resistor 82. This decreases the repetition rate at which the triggering pulses are generated at the outputs of the comparators 25, 26 henced the rate at which the flip-flop 28 changes state. Therefore, the electrical output pulses supplied via lead 32 to the transducer circuitry of block 27 are generated at a continually reducing frequency to some predetermined frequency lower than the established base frequency. This enables a gradual automatic decrease in the pitch of the sound generated by the transducer means 28, as previously described.

The transducer means 28 may be a sound reproducer or such as a loud speaker or a telephone receiver. In such transducers, electrical coils mechanically coupled to a diaphram act in cooperation with an electrically coupled magnet to produce vibration of the diaphram to generate sound waves. Similarly, a transducer to the type using a solenoid a tap a diaphram to produce sound may also be used with minor modification to the driver circuitry of block 27. Similarly, any type of electrically driven vibratory transducer may be used which is capable of generating sound waves in the normal frequency range of the average human voice.

In the preferred embodiment of the present invention, the pulse-generating circuit 24 may be a free-running multi-vibrator such as may be formed using a standard integrated circuit designated commericially as IC No. 55 or MC 1555. Normally, the component values in the RC circuit 25 are adjusted to produce a frequency of output pulses of about 90-120 cycles per second for men or 110-140 cycles per second for a woman, as desired. As disclosed hereinabove, the circuitry permits readjustment of the basic tone above and below the initially established rate if desired by changing the RC time constants involved. Furthermore, electrical output signals having waveforms other than square waves, such as saw tooths or sine waves may also be used but corresponding changes in the tonal qualities of the generated sound may result.

With this detailed description of the specific apparatus used to illustrate the prime embodiment of the present invention and the operation thereof, it will be obvious to those skilled in the art that various modifications can be made in the circuit of the present invention without departing from the spirit and scope thereof which is limited only by the appended claims.

I claim:

1. An artificial larnyx for enabling persons who have had their larnyx removed or the like to be able to speak comprising:
    first comparator means having first and second inputs and a comparator output, said first input being adapted to receive a first reference signal and said second input being adapted to receive a monitored signal for comparison with said first reference signal, said first comparator means being responsive to the detection of a pre-determined relationship between said monitored signal and said first reference signal for outputting a first triggering signal;
    second comparator means having first and second inputs and a comparator output, said first input being adapted to receive a second reference signal and said second input being adapted to receive said monitored signal for comparison with said second reference signal, said second comparator means being responsive to the detection of a second predetermined relationship between said monitored signal and said second reference signal for outputting a second triggering signal;

power supply means;

voltage divider means coupled between said power supply means and ground and having first and second voltage taps, said first voltage tap being coupled to the first input of said first comparator means for normally establishing said first reference signal and said second voltage tap being coupled to said first input of said second comparator means for normally establishing said second reference signal;

bistable means responsive to the generation of said first triggering signal for signal for assuming a first electrical state and responsive to the generation of said second triggering signal for switching to the opposite electrical state, the output of said bistable means being a train of electrical pulses whose frequency is determined by the rate at which said first and second triggering signals are generated by said first and second comparator means;

frequency stabilization means coupled to the output of said bistable means for receiving said generated train of electrical pulses and isolating said pulses from fluctuations due to variations in the load;

switching means coupled to the output of said bistable means and responsive to said bistable means being in said first state for switching to a conductive state and responsive to said bistable means being in said opposite state for switching to a non-conductive state;

first RC circuit means including a charging capacitor coupled between said power supply ground for supplying said monitored signal to the second input of said first and second comparator means, said RC circuit means responsive to the non-conductive of said switching means for charging said charging capacitor to increase the value of said monitored signal and responsive to said switching means being in the conductive state for discharging said capacitor and decreasing the value of said monitored signal such that the RC time constant of said first RC circuit means establishes the normal frequency at which said first and second triggering signals and therefore said train of electrical output pulses is generated;

a vibratory transducer means for generating sound waves which can be articulated in a person's mouth for speech purposes;

means responsive to the train of electrical pulses from said isolation means for driving said vibratory transducer means at a frequency determined by the frequency of state changes of said bistable means; and pitch change circuit means having an output node coupled to said voltage divider means for supplying a frequency control signal thereto for varying the value of said first and second reference signals so as to vary the frequency at which said first and second triggering signals and therefore said train of electrical output pulses are generated, said pitch change circuit means including a second RC circuit means for establishing a predetermined rate at which said frequency control signal varies and manually-operable switching means for selecting the direction in which said variation occurs at said established predetermined rate.

2. The artificial larynx of claim 1 wherein said second RC circuit means includes a first circuit branch including a first resistive means connected between said power supply means and said output node, a first capacitor connected in parallel with said first circuit branch between said power supply means and said output node, a second circuit branch including a second resistive means connected between said output node and ground, a second capacitor connected inparallel with said second circuit branch between said output node and ground, the values of said first and second resistive means and said first and second capacitors establishing said predetermined rate at which the frequency control signal at said output node varies, and wherein said manually-operable switching means includes a first manually-operated switching means connected in said first circuit branch in series with said first resistive means, said second RC circuit means being responsive to the closure of said first manually-operable switching means for increasing the value of said frequency conrol signal at said predetermined established rate and a second manually-operable switching means connected in said second circuit branch in series with said second resistive means, said second RC circuit mans being responsive to the closure of said second manually-operable switching means for decreasing the value of said frequency control signal at said predetermined established rate.

3. The artificial larynx of claim 2 wherein at least one of said first and second resistive means includes means for varying the value of the resistance thereof for changing the RC time constant of said pitch change circuit means so as to selectively alter said predetermined established rate.

4. The artificial larynx of claim 1 wherein said first RC circuit means for establishing the normal frequency at which said train of electrical output pulses is generated includes means for varying the rate at which said charging capacitor charges and discharges to vary said monitored signal so as to selectively increase and decrease the frequency of generation of said first and second triggering signals and therefore the normal frequency at which said train of electrical output pulses is generated.

5. The artificial larynx of claim 4 wherein said first RC circuit means includes resistive means connected in series between said power supply means and said charging capacitor, said resistive means including a first branch having a resistor of a first value therein and a second branch in parallel with said first branch and having a resistor of a lessor value therein, said resistive means further including switching means for selecting on of said branches to complete a series path between said power supply means and said charging capacitor, the selection of one of said branches establishing a basic frequency corresponding to the average fundamental frequency of a man's voice and the selection of the other of said branches establishing a basic frequency corresponding to the average fundamental frequency of a woman's voice.

6. The artificial larynx of claim 1 further characterized in that said driving means includes a switching means connected in a series current path with power supply means and said vibratory transducer means, said switching means being coupled to the output of said isolation means and being responsive to the train of electrical output pulses therefrom for driving said vibratory transducer means at a frequency predetermined by the frequency of generation of said train of electrical output pulses and variable impedance means in series with said switching means and said vibratory transducer means for controlling the volume of the sound generated by said vibratory transducer means.

7. The artificial larynx of claim 6 wherein said variable impedance mens includes first and second parallel branches connected in series with said switching means, the resistance of one of said paths being greater than the resistance of the other of said paths and manually-operable switching means for selecting one or the other of said paths so as to produce a corresponding low volume or high volume output from said vibratory transduce means.

8. The artificial larynx of claim 1 wherein said vibratory transducer means includes inductive means and said larynx includes capacitive means coupled in parallel across said inductive means for producing desireable harmonics into the audio output form said vibratory transducer means.

9. In an artificial larynx having means for generating electrical pulses at a predetermined frequency in the average fundamental frequency range of the human voice, transducer means for vibrating at said predetermined frequency to generate sound waves which can be articulated in a person's speech cavities fo speaking purposes and means responsive to said electrical pulses for driving said transducer means, the improvement comprising RC circuit means for generating a frequency control signal whose value varies at a predetermined rate established by the RC time constant of said RC circuit means;

means coupling said frequency control signal to sid pulse-generating means such that the rate of change of the value of said control signal determines the rate at which the frequency of generation of said electrical pulses changes; and manually-operable switching means coupled to said RC circuit means for enabling a person to selectively increase the value of said control signal so as to increase the frequency of generation of said electrical pulses at said established predetermined rate and for enabling a person to selectively decrease the value of said control signal so as to decrease the frequency of generation of said pulses at said established predetermined rate thereby permitting said person to select a direction of inflection in the pitch of the sound articulated in his speech cavities.

10. The improved artificial larynx of claim 9 wherein said RC circuit means includes a first circuit branch having resistive means therein connected between a power supply and a frequency control signal output node, a second circuit branch having a capacitive means therein connected in parallel across said first circuit branch between said power supply and said output node, a third circuit branch having resistive means therein connected between said output node and ground, and a fourth circuit branch having a capacitive means therein connected in parallel across said third circuit branch between said output node and ground, the values of said first and second resistive means and said first and second capacitive means determining the RC time constant of said RC circuit means and therefore establishing the predetermined rate at which said frequency control signal produced at said output node increases and decreases in value, said switching means including a first manually-operable switch connected in series in said first circuit branch such that the closure thereof initiates the charging of the capacitive means of said fourth circuit branch thereby increasing the value of said frequency control signal at said output node and a scond manually-operable switch in series with said third circuit branch for completing a current path to discharge the capacitive means of said second circuit branch to decrease the value of said fequency control signal at said output node thereby enabling said person to determine the direction of pitch change by selecting which of said first and second switches are to be closed.

11. The improved artificial larynx of claim 9 wherein said RC circuit means includes a first series path coupled between a power supply means and ground, said first circuit path including a resistive means and a charging capacitor, one plate of said charging capacitor being coupled to ground and an output node being provided that the junction of said resistive means and said charging capacitor for outputting said frequency control signal, the values of said resistive means and said charging capacitor establishing the RC time constant of said series circuit thereby establishing a predetermined rate at which the value of said frequency control signal varies; and wherein said manually-operable switching means includes a manually-operable switch coupled into said first series circuit, the closure of said switch completing a circuit path between said power supply means and ground for charging said charging capacitor and increasing the value of said frequency control signal at said output node at the predetermined rate determined by the established RC time constant of said series circuit.

12. The improved artificial larynx of claim 9 wherein said RC circuit means includes a series circuit path coupled between said a power supply means and ground, said series circuit path including a charging capacitor having one plate coupled to said power supply and its other plate coupled to a frequency control signal output node, said node being coupled through a resistive means to ground, the values of said resistive means and said charing capacitor establishing the RC time constant of said series circuit and therefore the predetermined rate at which the value of said frequency control signal varies; and wherein said manually-operable switching means includes a manually-operable switch connected in said series path such that the closure of said switch completes an electrical circuit between said charging capacitor and ground for discharging said charging capacitor through said resistive means to decrease the value of said frequency control signal at the predetermined rate established by the RC time constant of said series circuit.

13. The improved artificial larynx of claim 10 wherein at least one of the resistive means of said first branch and the resistive means of said third branch may be selectively varied to change the RC time constant of said RC circuit means thereby varying said predetermined established rate at which the value of said frequency control signal increases and decreases.

14. The improved artificial larynx of claim 9 further characterized in that said transducer means includes a coil and the improvement includes capacitive means connected across said coil for inroducing desireable harmonics into the sound generated by said transducer means to eliminate mechanically sounding monitones and produce a more human-sounding voice.

15. TAhe improved arificial larynx of claim 9 wherein said electrical pulse-generating means includes a second RC circuit means for normally establishing the frequency of generation of said electrical pulses in the average fundamental frequency range of a human voice and further includes means for varying the RC time constant thereof to selectively increase or decrease the normal fundamental frequency of generation of said pulses to suit the needs of the user.

16. The improved artificial larynx of claim 15 wherein said means for selectively increasing and decreasing the normal frequency of generation of said electrical pulses includes a parallel circuit branch having first impedance means of a first value in a first branch thereof for establishing an RC time constant to produce a lower frequency of generation of signals generally associated with a man's speech and a second parallel branch having second impedance means of a different value for producing a frequency of generation of said electrical pulses at a rate normally associated with a woman's voice, and wherein said second RC circuit means includes switching means for selecting one of said first and second branches.

17. The improved artificial larynx of claim 9 wherein said driving means includes means for selectively increasing and decreasing the volume of sound outputted from said vibratory transducer means.

18. An artificial layrnx comprising pulse-generating means coupled to a power supply for normally generating electrical pulses at a predetermined basic frequency generally in the normal range of fundamental frequencies for a human voice, said pulse generating means having an input normally responsive to the receipt of a reference signal for effecting the generation of said pulses at said predetermined basic frequency but further responsive to a frequency control signal whose value increases and decreases with time for increasing and decreasing the rate of generation of said electrical pulses to frequencies higher and lower than said predetermined basic frequency at a rate proportional to the rate of change of the value of said frequency control signal, transducer means coupled to said pulse generating means and responsive to the frequency of generation of said electrical pulses for producing sound waves in a person's speech cavitites which can be articulated for speach purposes, the frequency of generation of said pulses being directly related to the pitch of the sound produced, circuit means for establishing the rate at which the value of said frequency control signal automatically increases and decreases, and manually-operated switching means for selecting the direction in which the value of said frequency control signal automatically increases or decreases at said established rate.

19. The artificial larynx of claim 18 wherein said circuit means for establishing the rate at which the value of said frequency control signal automatically increases and decreases includes a first series path coupled between said power supply means and ground, said first series path including a resistive means and a charging capacitor, the juncture of said resisted means with said charging capacitor serving as an output node for said frequency control signal, the opposite plate of said capacitor means being coupled to ground, said circuit means further including a second series path coupled between said power supply means and ground, said second series path including a second charging capacitor and a second resistive means, the juncture of said second charging capacitor and said second resistive means corresponding to said output node and the opposite plate of said second charging capacitor being coupled to said power supply means; and wherein said manually-operable switching means includes a first manually operable switch interposed in said first series circuit such that the closure of said switch completes a current path between said source of potential and ground for charging said first charging capacitor so that the frequency control signal generated at said output node increases at a rate determined by the RC time constant of said first series circuit, and a second manual-operable switch interposed in said second series path for completing a discharge circuit between said second charging capacitor and ground through said second resistive means for discharging said capacitor and decreasing the value of said frequency control signal at said output node at a rate determined by the RC time constant of said second series path.

20. The artificial larynx of claim 18 wherein said pulse generating means includes:
a first comparator having first and second inputs and an output, said first comparator being responsive to the equality of the signals present at said first and second inputs for generating a first triggering signal at the output thereof;
a second comparator means having first and second inputs and an output, said second comparator means being responsive to the equality of the signals present at said first and second inputs for generating a second triggering signal at the output thereof;
flip-flop means having its inputs coupled to the outputs of said first and second comparator means for being driven to a first state in response to the generation of said first triggering signal and to the opposite state in response to the generation of said second triggering signal such that the output thereof is a series of electrical pulses whose frequency is determined by the frequency at which said first and second triggering signals are generated by said first and second comparator means respectively;
voltage divider means coupled between a source of potential and ground, said voltage divider means having a first output coupled to said first input of said first comparator means for supplying a first reference signal thereto and a second output coupled to the first input of said second comparator means for supplying a second reference signal thereto, said first and second reference signals normally controlling the rate of generation of said first and second triggering signals and therefore establishing said predetermined basic frequency of generation of output pulses from said flip-flop means; and
RC circuit means coupled between said power supply and ground said RC circuit means including a charging capacitor having one plate grounded and a first resistive means coupled between the opposite plate of said charging capacitor and said power supply, the junction of said first resistive means and said charging capacitor being coupled to the second inputs of said first and second comparator means for supplying a monitored signal thereto to be compared with said first and second reference signals; and switching means coupled between said opposite end of said first resistive means and ground, said switching means bing responsive to the output of said flip-flop means for conducting to discharge said charging capacitor through said resistive means when said flip-flop means is in said on state and for switching to a non-conductive state to allow the charging of said charging capacitor from said power supply means when said flip-flop means is in said opposite state, the RC time constant of sid RC circuit means establishing the rate at which said charging capacitor charges and discharges thereby establishing the rate of variation of said monitored signal such that when said monitored signal is equal to said first reference signal, said first comparator means generates said first triggering signal to place said flip-flop means and said first state and cause said switching means to conduct so as to discharge said charging capacitor and cause said monitored signal to fall until said monitored signal is equal to said second reference signal thereby causing said second comparator means to generate said second triggering signal to switch said flip-flop means to said opposite state such that the frequency of generation of said electrical output pulses is determined by the rate at which said triggering puses are produced, said frequency control signal being supplied to said first output of said voltage divider means for overriding said normal first and second reference signals so as to increase and decrease the value of said first and second reference signal as the value of said frequency control signal increases and decrease thereby increasing and decreasing the rate at which said first and second triggering signals are generated and therefore causing said electrical pulses to be generated at a rate greater or lower than said predetermined basic frequency.

* * * * *